(12) United States Patent
Powers

(10) Patent No.: US 12,427,054 B2
(45) Date of Patent: *Sep. 30, 2025

(54) ROLLABLE DEVICE WITH FEATURES AIDING SOFT TISSUE RELEASE AND MUSCLE LOOSENING

(71) Applicant: Thomas Martin Powers, Edina, MN (US)

(72) Inventor: Thomas Martin Powers, Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/742,352

(22) Filed: Jun. 13, 2024

(65) Prior Publication Data

US 2024/0325194 A1    Oct. 3, 2024

Related U.S. Application Data

(63) Continuation of application No. 18/448,447, filed on Aug. 11, 2023, now abandoned, which is a
(Continued)

(51) Int. Cl.
*A61F 7/00* (2006.01)
*A61H 15/00* (2006.01)
*A61H 15/02* (2006.01)

(52) U.S. Cl.
CPC ............. *A61F 7/007* (2013.01); *A61H 15/02* (2013.01); *A61F 2007/0071* (2013.01); *A61F 2007/0078* (2013.01); *A61F 2007/0086* (2013.01); *A61F 2007/0093* (2013.01); *A61F 2007/0096* (2013.01); *A61H 2015/0042* (2013.01); *A61H 2201/0119* (2013.01);
(Continued)

(58) Field of Classification Search
CPC ................ A61H 15/00; A61H 15/0078; A61H 15/0092; A61H 2015/0007; A61H 2015/0014; A61H 2015/0021; A61H 2015/0042; A61H 2015/0078; A61H 2201/0228; A61H 2201/0235; A61H 2201/0207; A61H 2201/0119; A61H 2201/0153; A61H 23/02; A61F 2007/0071; A61F 2007/0078
See application file for complete search history.

(56) References Cited

U.S. PATENT DOCUMENTS 1,936,022 A    11/1933    Hunt
4,021,769 A    5/1977    Edin et al.
(Continued)

*Primary Examiner* — Colin W Stuart
*Assistant Examiner* — Douglas Y Sul
(74) *Attorney, Agent, or Firm* — McHale & Slavin, P.A.

(57) ABSTRACT

A rollable apparatus includes a housing being annular in shape, a heating element mounted about the exterior of the housing, a vibration-inducing motor mounted in the interior of the housing and attached thereto, and a set of batteries mounted in the interior of the housing. The set of batteries is provided for powering the heating element to control the temperature of the housing and for powering the vibration motor to induce oscillatory motion in the housing. The apparatus also includes a set of user controls mounted so as to be accessible at the exterior of the housing, a front cover removably mounted so as to form a portion of the exterior of the housing at one end thereof, and a skin of pliable cushioning material covering the housing.

19 Claims, 13 Drawing Sheets

Related U.S. Application Data continuation of application No. 17/816,815, filed on Aug. 2, 2022, now abandoned, which is a continuation of application No. 16/867,201, filed on May 5, 2020, which is a continuation of application No. 15/169,657, filed on May 31, 2016, now Pat. No. 10,682,252.

(60) Provisional application No. 62/169,291, filed on Jun. 1, 2015.

(52) U.S. Cl.
CPC ............... *A61H 2201/0188* (2013.01); *A61H 2201/0207* (2013.01); *A61H 2201/0228* (2013.01); *A61H 2201/1207* (2013.01); *A61H 2201/1261* (2013.01); *A61H 2201/1284* (2013.01); *A61H 2201/1671* (2013.01); *A61H 2201/5007* (2013.01); *A61H 2201/5082* (2013.01); *A61H 2201/5097* (2013.01); *A61H 2205/065* (2013.01); *A61H 2205/081* (2013.01)

(56) References Cited

U.S. PATENT DOCUMENTS

| | | | |
|---|---|---|---|
| 4,116,233 A | 9/1978 | Scaduto | |
| 4,175,551 A | 11/1979 | D'Haenens et al. | |
| 5,413,551 A * | 5/1995 | Wu | A61H 15/00 601/131 |
| 5,554,102 A * | 9/1996 | Chiou | A61H 15/0092 601/72 |
| 5,830,161 A * | 11/1998 | Cosmano | A61H 15/00 601/118 |
| 5,925,002 A | 7/1999 | Woolman | |
| 6,432,071 B1 | 8/2002 | Hsich | |
| 7,244,237 B2 | 7/2007 | Smith | |
| 7,399,285 B2 | 7/2008 | Stein | |
| 8,721,572 B1 | 5/2014 | Linder et al. | |
| 9,968,513 B1 * | 5/2018 | Marton | A61H 23/0263 |
| 10,682,252 B2 * | 6/2020 | Powers | A61F 7/007 |
| 2003/0131416 A1 | 7/2003 | Lee | |
| 2004/0138595 A1 | 7/2004 | Fang | |
| 2005/0015025 A1 | 1/2005 | Stein | |
| 2005/0070827 A1 * | 3/2005 | Lee | A61H 23/0263 601/57 |
| 2007/0060851 A1 | 3/2007 | Ferber et al. | |
| 2009/0051327 A1 | 2/2009 | Bohne | |
| 2009/0176635 A1 | 7/2009 | Brinson | |
| 2010/0274162 A1 | 10/2010 | Evans | |
| 2011/0071446 A1 | 3/2011 | Citrin | |
| 2012/0046579 A1 * | 2/2012 | Radl | A61H 11/00 601/46 |
| 2012/0265106 A1 | 10/2012 | Accardo et al. | |
| 2012/0265240 A1 | 10/2012 | Ganske et al. | |
| 2012/0323151 A1 | 12/2012 | Faussett | |
| 2013/0012848 A1 | 1/2013 | Forrest | |
| 2013/0090583 A1 | 4/2013 | Jung | |
| 2013/0231594 A1 | 9/2013 | Bennett | |
| 2013/0281892 A1 * | 10/2013 | Godfrey | A61H 1/00 601/70 |
| 2014/0012168 A1 | 1/2014 | Carlson | |
| 2016/0279018 A1 | 9/2016 | Egan et al. | |

\* cited by examiner

ROLLABLE DEVICE WITH FEATURES AIDING SOFT TISSUE RELEASE AND MUSCLE LOOSENING

PRIORITY CLAIM

In accordance with 37 C.F.R. 1.76, a claim of priority is included in an Application Data Sheet filed concurrently herewith. Accordingly, the present invention claims priority as a Continuation of U.S. patent application Ser. No. 18/448,447, entitled "ROLLABLE DEVICE WITH FEATURES AIDING SOFT TISSUE RELEASE AND MUSCLE LOOSENING", filed Aug. 11, 2023, which claims priority to U.S. patent application Ser. No. 17/816,815, entitled "ROLLABLE DEVICE WITH FEATURES AIDING SOFT TISSUE RELEASE AND MUSCLE LOOSENING", filed Aug. 2, 2022, which claims priority to U.S. patent application Ser. No. 16/867,201, entitled "ROLLABLE DEVICE WITH FEATURES AIDING SOFT TISSUE RELEASE AND MUSCLE LOOSENING", filed May 5, 2020, which claims priority to U.S. patent application Ser. No. 15/169,657, entitled "ROLLABLE DEVICE WITH FEATURES AIDING SOFT TISSUE RELEASE AND MUSCLE LOOSENING" filed May 31, 2016, which claims priority to U.S. Provisional Patent Application No. 62/169,291, entitled "ROLLABLE DEVICE WITH FEATURES AIDING SOFT TISSUE RELEASE AND MUSCLE LOOSENING", filed Jun. 1, 2015. The contents of the above referenced applications are incorporated herein by reference.

FIELD OF THE INVENTION

The present invention relates generally to the release of muscle tension, and more particularly, to a rollable apparatus incorporating both vibration and heating features aiding soft tissue release, muscle loosening, and or muscle activation.

BACKGROUND OF THE INVENTION

In the science of sports medicine, physiotherapy, and strength and conditioning there is a constant search for ways to improved range of motion, functional movement, blood flow, and relaxation of the body and, particularly, those areas prone to becoming overly tight due to overuse and stress. Of interest are devices that are particularly useful in the self myofascial release realm.

Accordingly, there remains a need in the art for an innovation that will provide a solution to the problems with the muscle function of the body in the aforementioned areas that remain unsolved.

SUMMARY OF THE INVENTION

The present invention is directed to an innovation that overcomes the deficiencies of the known art and the problems that remain unsolved by providing a rollable apparatus with features aiding soft tissue release and muscle loosening.

In one aspect of the present invention, a rollable apparatus includes:
a housing being annular in shape;
a heating element mounted about the exterior of the housing;
a vibration-inducing motor mounted in the interior of the housing and attached thereto;
at least one battery mounted in the interior of the housing for powering the heating element to heat the housing to a temperature level within a given temperature range and for powering the vibration-inducing motor to induce oscillatory motion in the housing; and
a set of user controls mounted on the housing to control the heating element and the vibration-inducing motor.

In another aspect, a microprocessor is mounted in the housing for receiving inputs from the set of user controls operated by a user to control respective operation of the heating element and vibration-inducing motor. A temperature sensor is provided in the housing for sensing and inputting temperature status of the heating element to the microprocessor for controlling operation of the heading element. The set of user controls is a set of user-operated push buttons for activating inputs to the microprocessor and a plurality of LED lights controlled by the microprocessor for indicating the status of the heating element and vibration-inducing motor. A battery fuel gauge is provided for indicating the status of battery electrical charge to the microprocessor, and a battery charger is operable for increasing the electrical charge of the battery.

In another aspect, the heating element includes an annular band and a plurality of arcuate strands attached to the band in a laterally spaced-apart array that matches an array of grooves formed in the exterior of the housing such that the heating element strands fit within the array of grooves formed in the housing exterior. Also, a skin of pliable cushioning material covers the housing and the heating element thereon.

In another aspect, the housing includes front and rear housing portions. The front housing portion has a rear annular rim and the rear housing portion has a front annular rim that faces toward and fits with the rear annular rim of the front housing portion. The rear housing portion also has a plurality of rear lugs formed on, and protruding radially inward from, the interior of the rear housing portion at angular and circumferentially-spaced relationships to one another and proximate the front annular rim such that the rear lugs terminate substantially flush with the front annular rim. The front housing portion also has a plurality of front lugs formed on, and protruding radially inward from, the interior of the front housing portion at angular and circumferentially-spaced relationships to one another and proximate the rear annular rim such that the front lugs terminate substantially flush with the rear annular rim and the front lugs on the front housing portion are alignable with the rear lugs on the rear housing portion when the front and rear housing portions are fitted to one another. The housing also includes a plurality of fasteners securing the aligned pairs of the front and rear lugs together and thereby detachably attaching the front and rear housing portions to one another.

In another aspect, the rollable apparatus includes:
a housing being annular in shape;
a heating element mounted about the exterior of the housing;
a vibration-inducing motor mounted in the interior of the housing and attached thereto;
at least one battery mounted in the interior of the housing for powering the heating element to heat the housing to a temperature level within a given temperature range and for powering the vibration-inducing motor to induce oscillatory motion in the housing;
a set of user controls mounted on the housing to control the heating element and the vibration-inducing motor;
a front cover removably mounted on the exterior of the housing so as to cover the set of user controls; and rear and front roller elements mounted to a rear end of the housing and to the front cover such that the front cover must be removed to gain access to the set of user controls.

In another aspect, a grip handle device is provided being detachable attachable to the rear and front roller elements to enable a user to grasp and carry the rollable apparatus.

In another aspect, a rollable apparatus includes:
a housing being annular in shape;
a heating element mounted about the exterior of the housing;
a vibration-inducing motor mounted in the interior of the housing and attached thereto;
at least one battery mounted in the interior of the housing for powering the heating element to heat the housing to a temperature level within a given temperature range and for powering the vibration-inducing motor to induce oscillatory motion in the housing;
a set of user controls mounted on the housing to control the heating element and the vibration-inducing motor;
a roller element mounted to one end of the housing; and
a cover mounted to an opposite end of the housing and having an opening recessed centrally therein through which to gain access to the set of user controls such that the cover need not be removed to access the set of user controls.

In another aspect, a glove handle device is provided being detachably attachable to the roller element at a respective one of the opposite ends of the housing for receiving a hand of a user to grasp and direct the rollable apparatus in contact with areas of the body of the user for application of a desired treatment thereto.

These and other aspects, features, and advantages of the present invention will become more readily apparent from the attached drawings and the detailed description of the preferred embodiments, which follow.

BRIEF DESCRIPTION OF THE FIGURES

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION OF THE INVENTION

Figure 1:
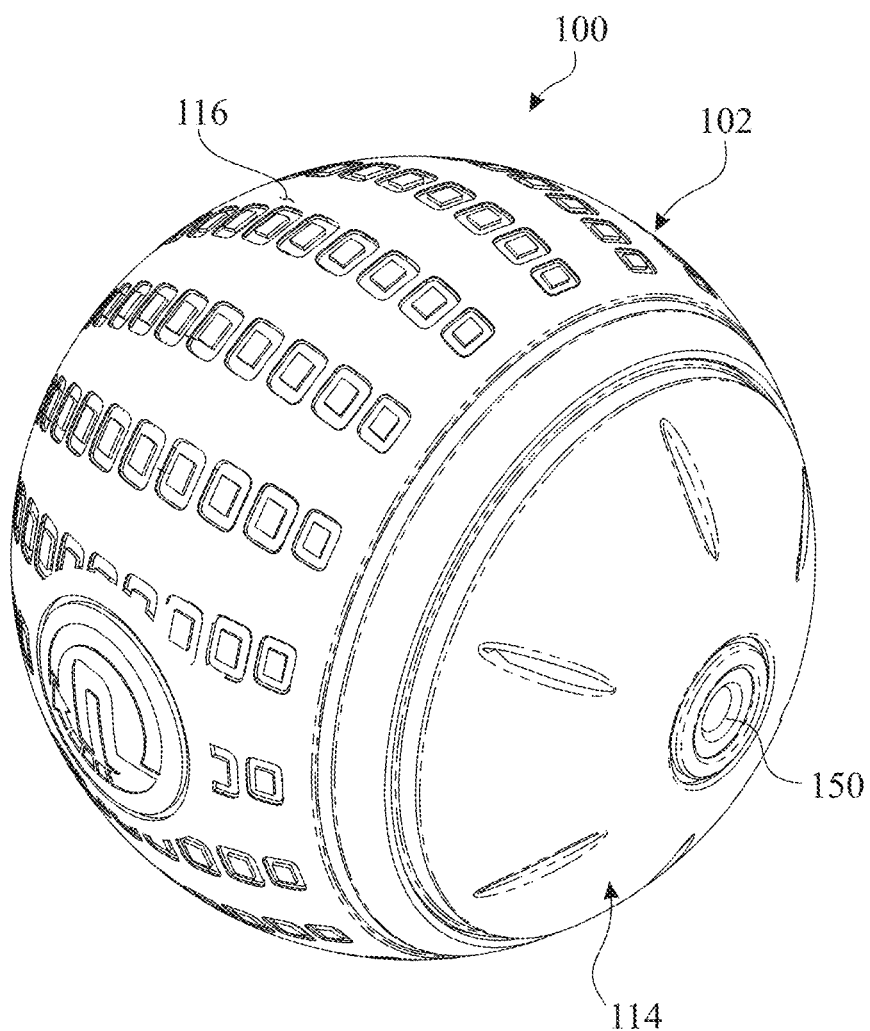
FIG. 1 presents an isometric assembly view of an exemplary embodiment of a rollable apparatus with features aiding soft tissue release and muscle loosening in accordance with aspects of the present invention.
Figure 2:
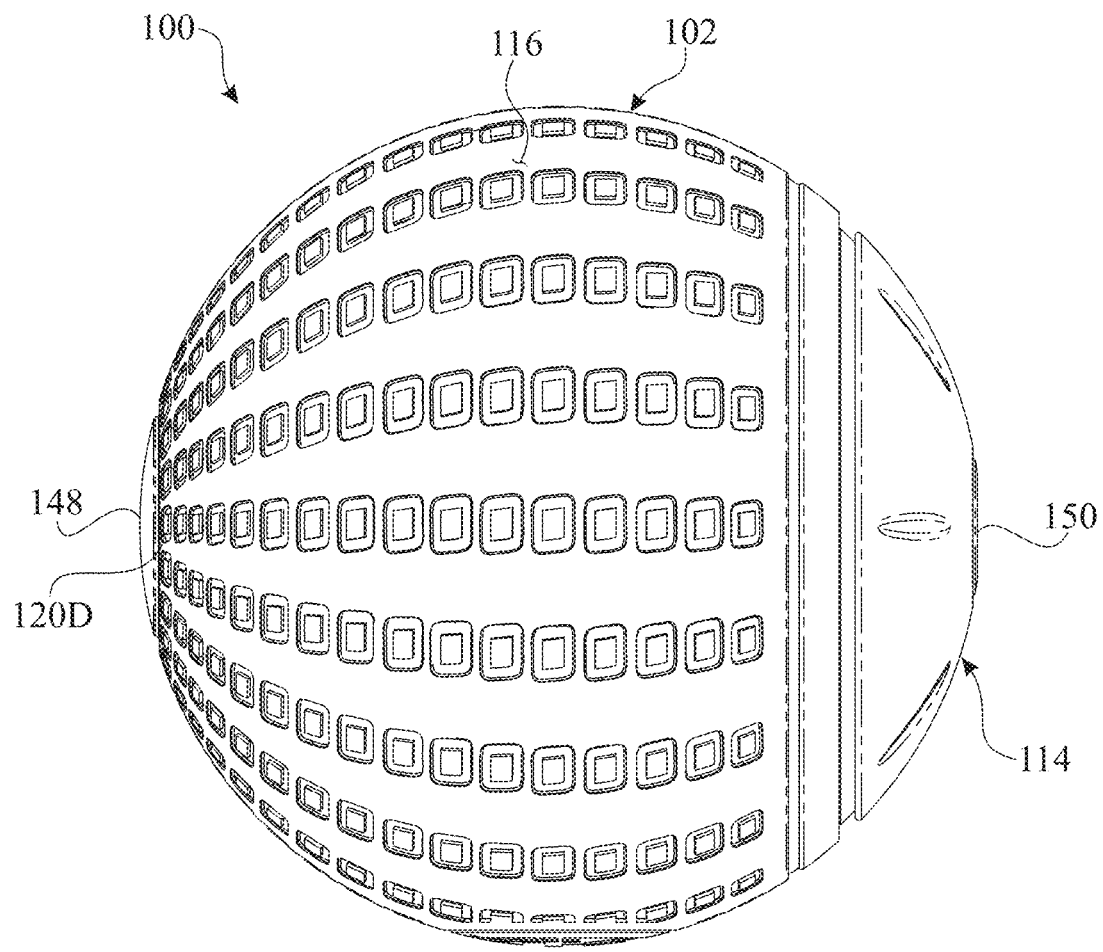
FIG. 2 presents a side elevation view of the rollable apparatus originally introduced in FIG. 1.
Figure 3:
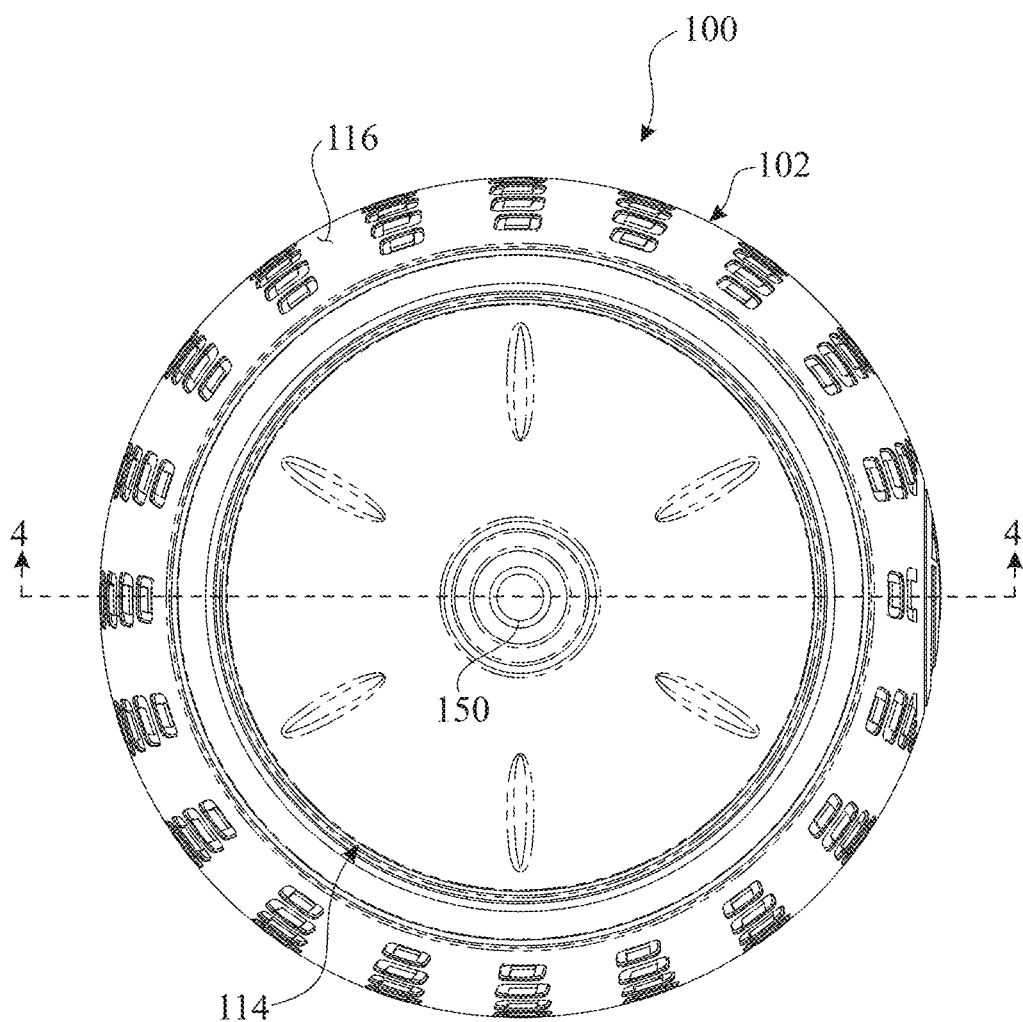
FIG. 3 presents a front elevation view of the rollable apparatus originally introduced FIG. 1.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-6, there is illustrated an exemplary embodiment of a rollable apparatus, generally designated 100, in accordance with aspects of the present invention. The rollable apparatus 100 is configured and operable to aid in soft tissue release and muscle loosening, due primarily to its spherical shape along with its ability to oscillate and generate heat. The rollable apparatus 100 includes a housing 102, a heating element 104 mounted about the exterior of the housing 102, a vibration-inducing motor 106 and at least one and preferably a set of batteries 108, such as, for example, Lithium ion type batteries, mounted in the interior of the housing 102 by a sub-housing 110, and a set of user push button controls 112 on the housing 102. Also, a front cover 114 mounted on the exterior of the housing 102 is removable to gain access to the user push button control set 112. The set of batteries 108 are for powering the heating element 104 and the vibration-inducing motor 106. The device 100 also includes a skin 116 of pliable or cushioning material covering the housing 102.

Figure 6:
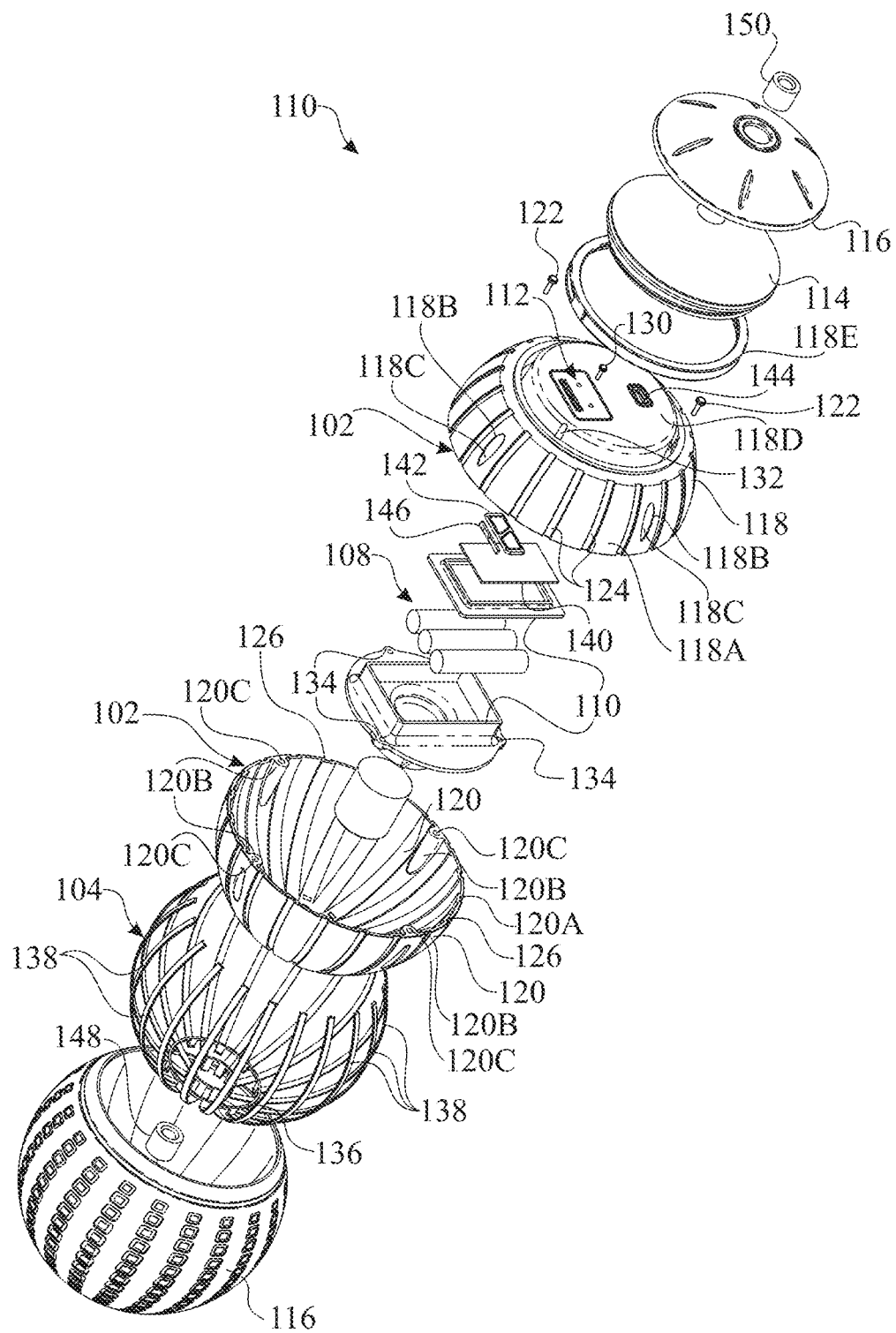
FIG. 6 presents an isometric exploded view of the rollable apparatus originally introduced in FIG. 1.

More particularly, as best seen in FIG. 6, the housing 102, being configured in a spherical shape by way of example but not limitation, has front and rear housing portions 118 and 120, respectively. The front housing portion 118 has a rear annular rim 118A, and the rear housing portion 120 has a front annular rim 120A that faces toward and fits with the rear annular rim 118A of the front housing portion 118. The rear housing portion 120 also has a plurality of rear lugs 120B, such as four in number, by way of example but not limitation being formed on, and protruding radially inward from, the interior of the rear housing portion 120 at angular and circumferentially-spaced relationships to one another and proximate the front annular rim 120A, such that the rear lugs 120B terminate substantially flush with the front annular rim 120A. The front housing portion 118 has a plurality of front lugs 118B, such as four in number, by way of example but not limitation being formed on, and protruding radially inward from, the interior of the front housing portion 118 at angular and circumferentially-spaced relationships to one another and proximate the rear annular rim 118A such that front lugs 118B terminate substantially flush with the rear annular rim 118A and the front lugs 118B on the front housing portion 118 are alignable with the rear lugs 120B on the rear housing portion 120 when the front and rear housing portions 118, 120 are fitted to one another. Threaded portions of fasteners 122, such as screws, may be inserted through apertures 118C in the front lugs 118B and threaded into threaded openings 120C tapped in the rear lugs 120B in order to detachably attach the front and rear housing portions 118, 120 to one another.

Figure 4:
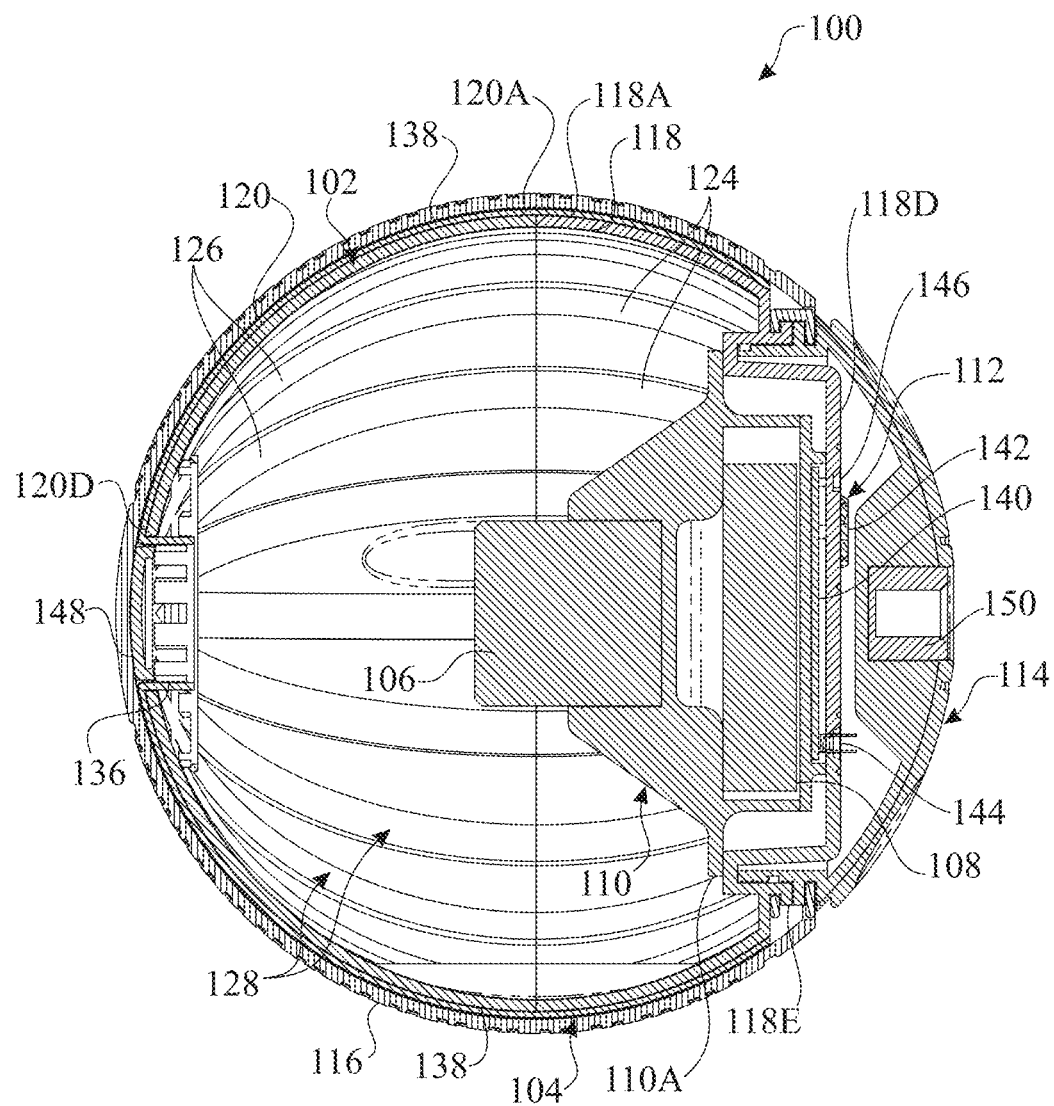
FIG. 4 presents a diametrically sectioned view of the rollable apparatus taken along section line 4-4 in FIG. 3.
Figure 5:
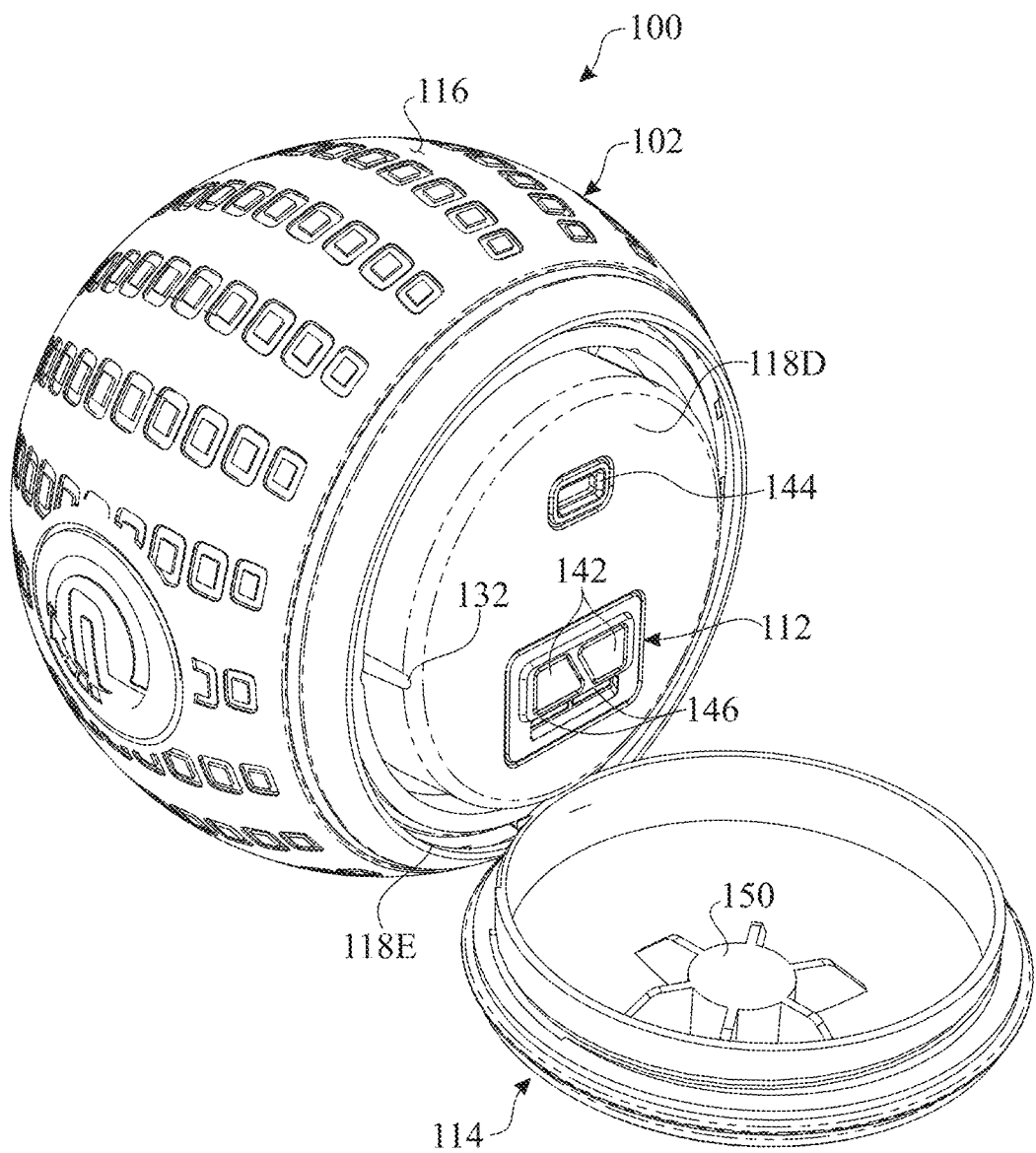
FIG. 5 presents an isometric view of the rollable apparatus similar to that of FIG. 1, except that a cover has been removed from an end of the rollable apparatus.

Also, as best seen in FIGS. 4-6, the rear housing portion 120 of the housing 102 has a rear end 120D, and the front housing portion 118 of the housing 102 has a truncated front end 118D formed with a threaded annular rim 118E. To gain access to the set of user push button control set 112 located on the truncated front end 118D, the front cover 114 is removably mounted on the housing 102 by the threaded annular rim 118E on the truncated front end 118D of the housing 102. Further, the exteriors of the front and rear housing portions 118, 120 of the housing 102 have respective groove portions 124, 126 recessed therein and being laterally spaced apart from each other. The groove portions 124, 126 align end-to-end with one another when the front and rear housing portions 118, 120 are attached to one another by the fasteners 122 such that together the groove portions 124, 126 form an array of grooves 128 that extend from the rear end 120D of the rear housing portion 120 to truncated front end 118D of the front housing portion 118.

As best seen in FIGS. 4 and 6, the sub-housing 110 of the apparatus 100 detachably attaches to the interior side of the truncated front end 118D of the front housing portion 118 of the housing 102 by fasteners 130 that seat in slots 132 in the truncated front end 118D and thread into apertures 134 in the peripheral rim 110A of the sub-housing 110. The sub-housing 110 supports the vibration-inducing motor 106 and the set of batteries 108, such that the latter provide electrical power to the heating element 104 and the vibration-inducing motor 106 via electrical connections associated with the sub-housing 110. The heating element 104, mounted about the exterior of the housing 102, may take the form of an annular band 136 and a plurality of arcuate strands of wires 138 attached to the band 136 in a laterally spaced-apart array that matches the array of grooves 128 in the exterior of the housing 102, such that the heating element strands of wires 138 fit or are embedded within the array of grooves 128 of the exterior of the housing 102. The internal motor 106 has the capability to oscillate at different speeds or frequencies. The vibrations are transmitted from the motor 106 to the housing 102 via the sub-housing 110 and the truncated front end 118D of the front housing portion 118 of the housing 102.

Figure 8:
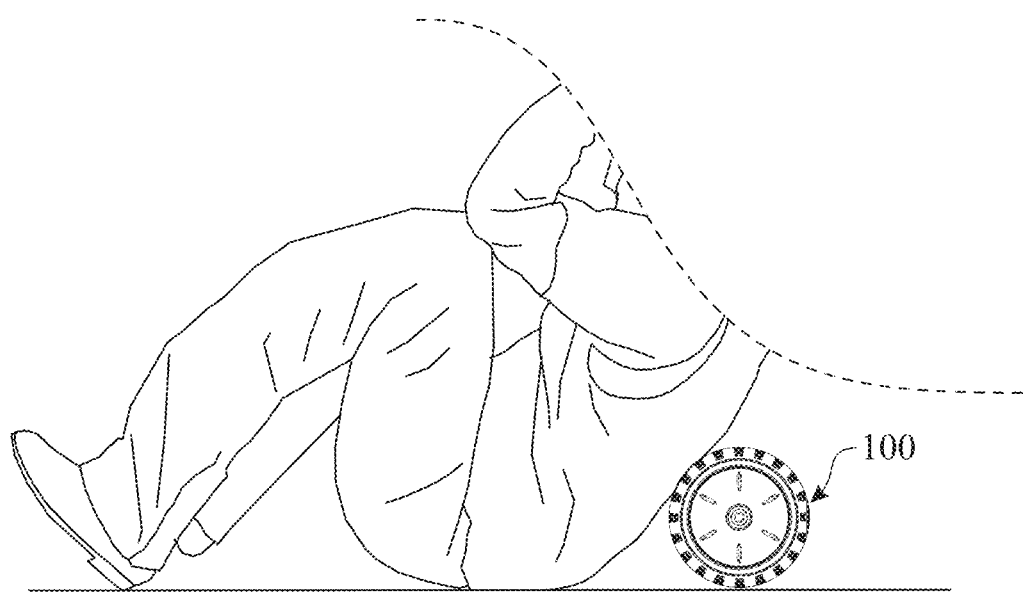
FIG. 8 presents a view of the rollable apparatus during use.
Figure 9:
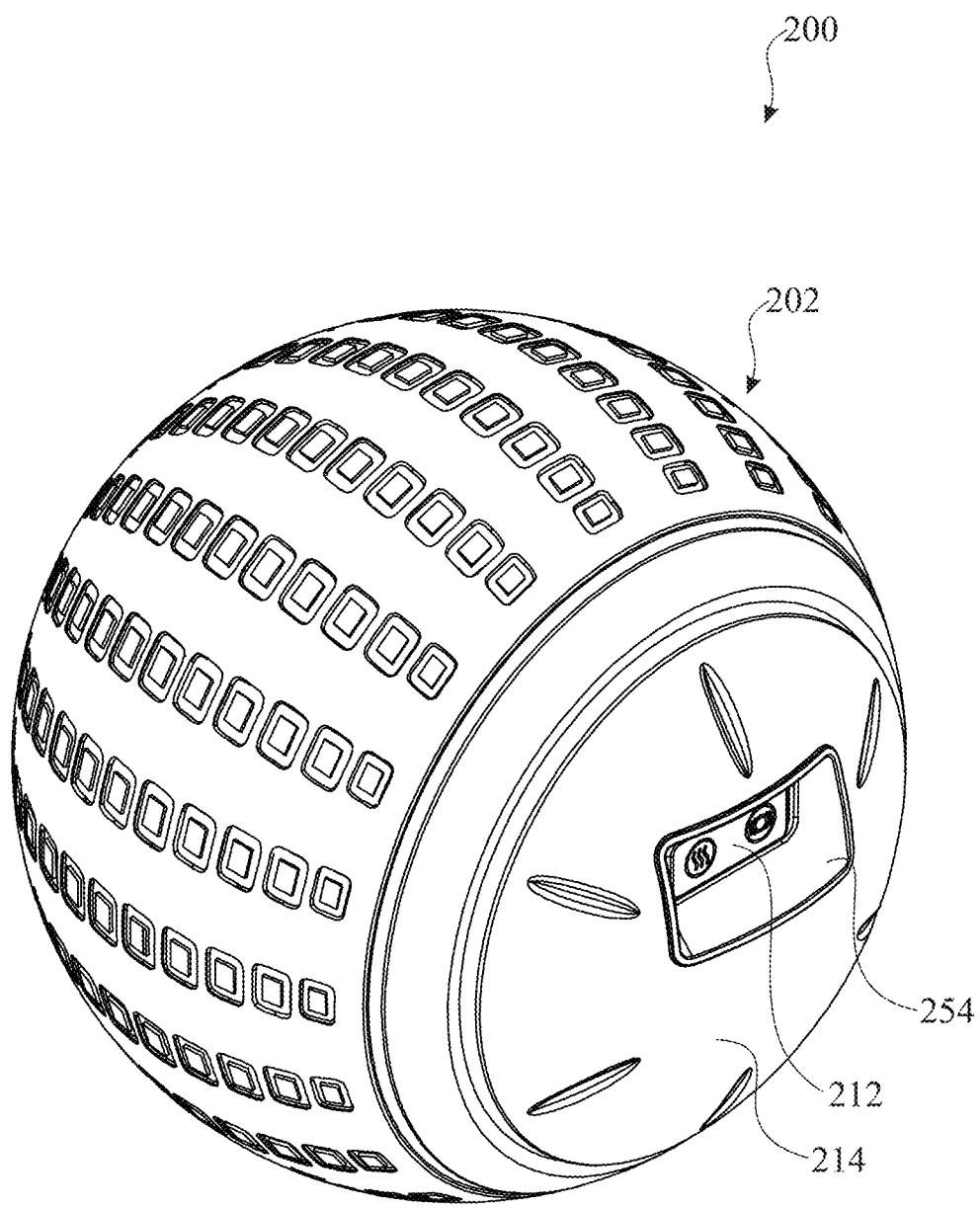
FIG. 9 presents an isometric assembly view of a slightly modified implementation of the rollable apparatus of FIG. 1.

Furthermore, the apparatus 100 is equipped with a printed circuit board (PCB) 140 mounted to the sub-housing 110 and at least one on/off power switch or button 142 of the push button control set 112 and a micro USB 144 mounted to the truncated front end 118D of the housing 102 to selectively turn the heating element 104 on and off, to selectively provide heat and to control a charge level. Light Emitting Diode (LED) lights 146 are also preferably mounted to the truncated front end 118D of the housing 102 to indicate oscillation intensity, heating element status and charge level. The skin 116 of pliable or cushioning material covering the housing shell 102 may be in the form of an outer lining of polyurethane foam, or silicone or rubber material, for example, imparting comfort to the person using the device 100, as shown in FIG. 8. The heating element 104, for example, in the form of strands of wires 138, is located underneath the outer skin 116 of pliable or cushioning material. The internally-disposed set of batteries 108 may be rechargeable through a recessed port in the truncated front end 118D of the housing 102.

Figure 7:
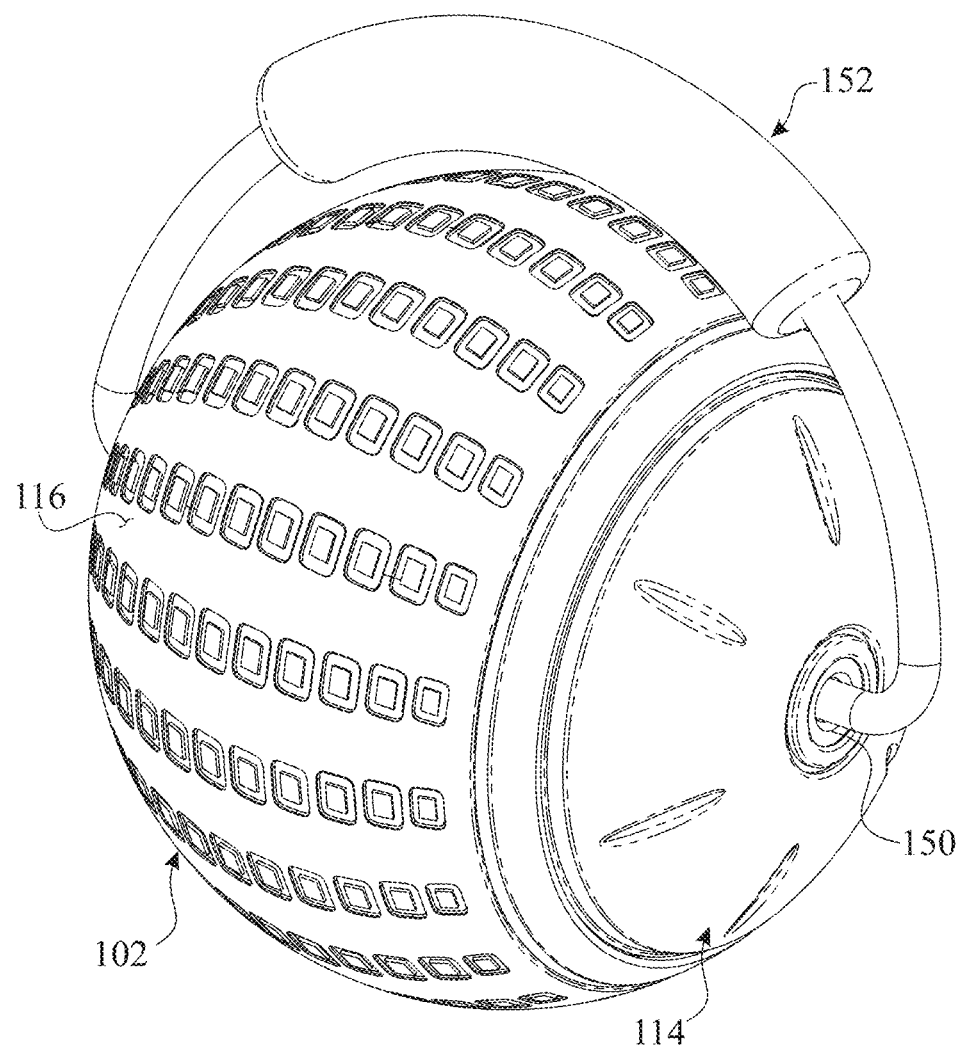
FIG. 7 presents an isometric view of the rollable apparatus similar to that of FIG. 1, except that a grip handle device is detachably attached at the opposite ends of the rollable apparatus.

Referring FIGS. 4 and 7, it can be seen that rear and front roller elements 148, 150 may be mounted to rear end 120E of the housing 102 and to the front cover 114. Also, a grip handle device 152 may be deployed in conjunction with the rollable apparatus 100 by being detachably attached to the rear and front roller elements 148, 150 at the respective opposite ends of the rollable apparatus 100. The grip handle device 152 is employed by a user to more conveniently grasp and carry the rollable apparatus 100. Also, in FIG. 8 the rollable apparatus 100 is shown in one position of use by a user.

Figure 10:
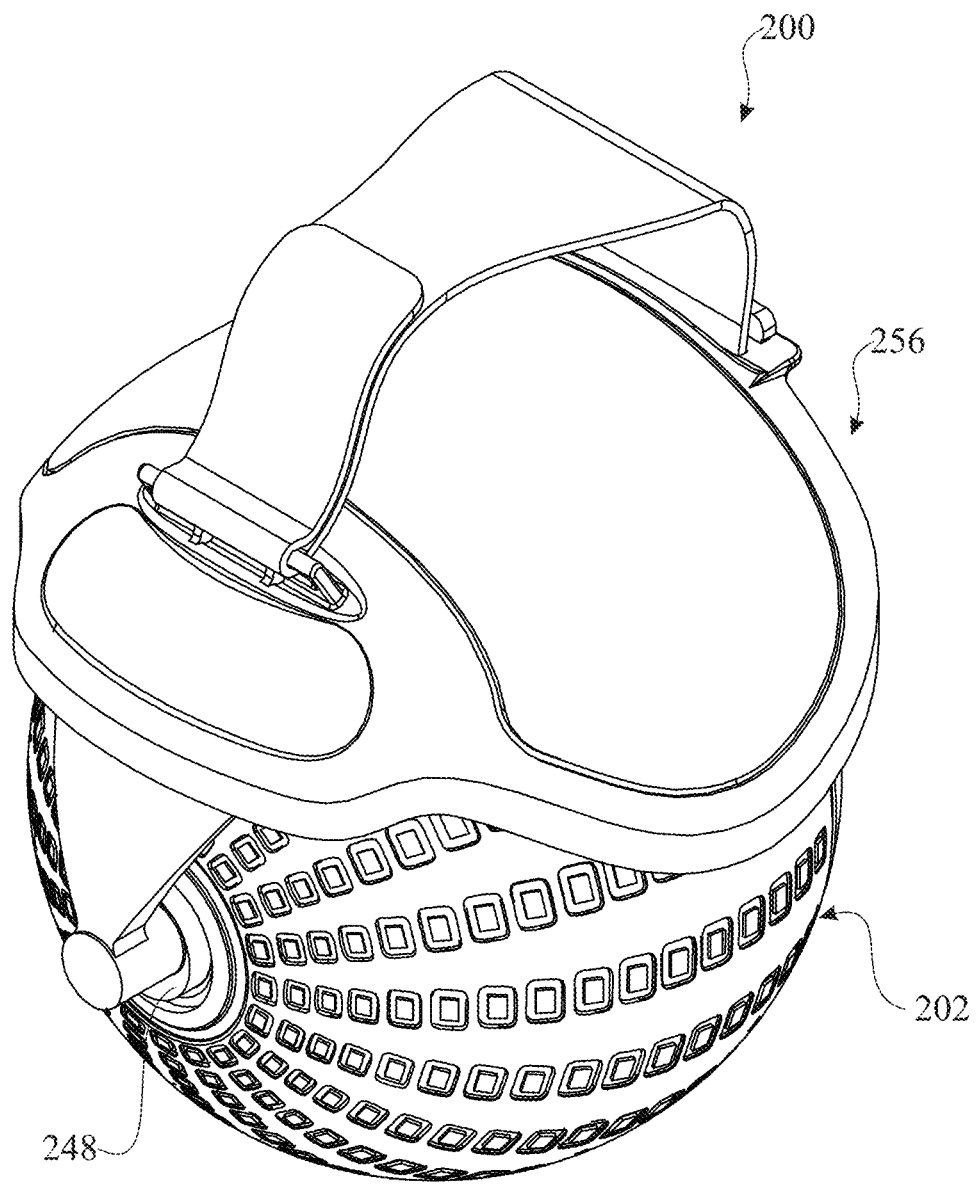
FIG. 10 presents an isometric view of the rollable apparatus similar to that of FIG. 9, except that a glove handle device is detachably attached at one of the opposite ends of the rollable apparatus.
Figure 11:
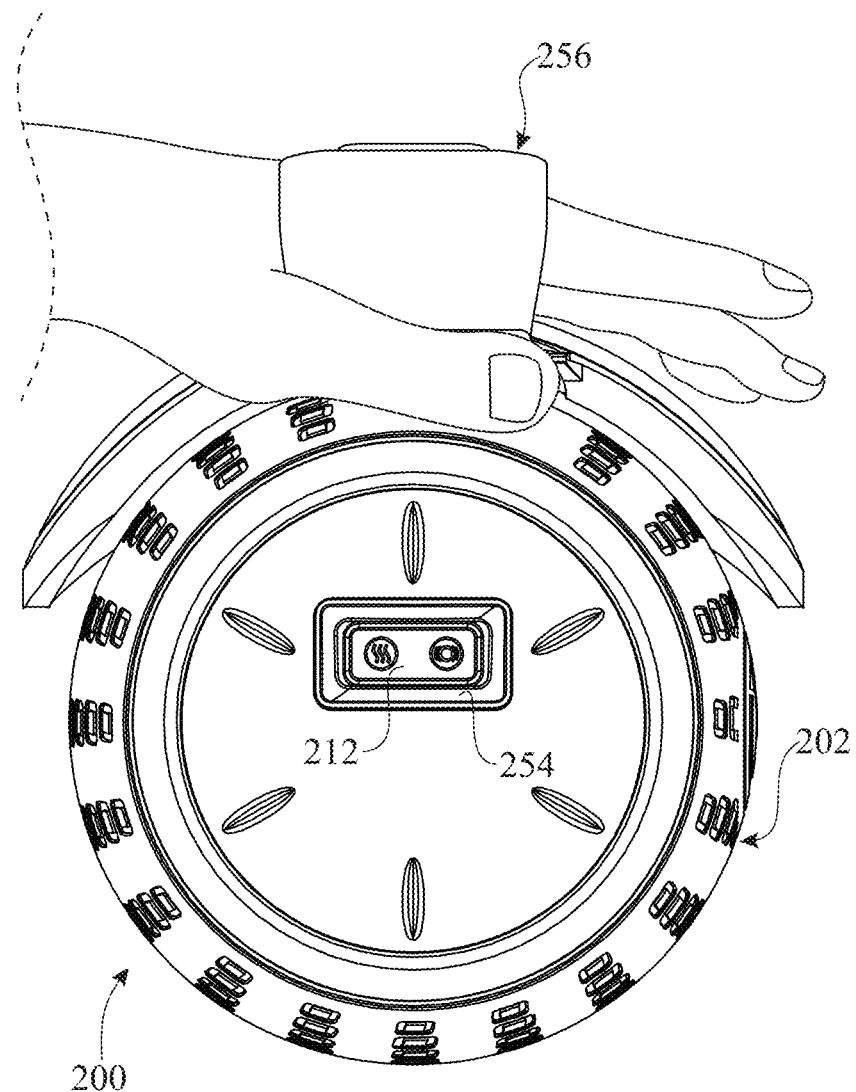
FIG. 11 presents a side elevation view of the rollable apparatus of FIG. 10 showing a user's hand inserted into the glove handle device.

Referring now to FIGS. 9-12, there is illustrated a rollable apparatus, generally designated 200, which is slightly modified implementation of the rollable apparatus 100 in accordance with other aspects of the present invention. The rollable apparatus 200 is configured with substantially the same structural and operational features as described above with respect to rollable apparatus 100 to aid in soft tissue release and muscle loosening, due primarily to its spherical shape along with its ability to oscillate and generate heat. Those of the features of the rollable apparatus 200 seen in FIGS. 9-12 being like those of the rollable apparatus 100 are numbered the same except preceded by the numeral '2'. Reference is directed to the above description of the structural and operational features of the rollable apparatus 100 for gaining an understanding of the rollable apparatus 200, which is substantially similar thereto. The only significant difference between the two rollable apparatuses 100,200 is the rollable apparatus 200 does not employ the front roller element 150 in its removable front cover 214. Instead the front cover 214 has a portal or opening 254 recessed centrally therein through which to gain access to the set of user controls 212. As a result the front cover 214 need not be removed to access the set of user controls 212. Also, as shown in FIGS. 10 and 11, a glove handle device 256 may be detachably attached to the rear roller element 248 at a respective one of the opposite ends of the housing 202 for receiving a hand of a user to more conveniently grasp and direct the rollable apparatus 200 in contact with areas of the user's body for application of the desired treatment thereto.

Figure 13:
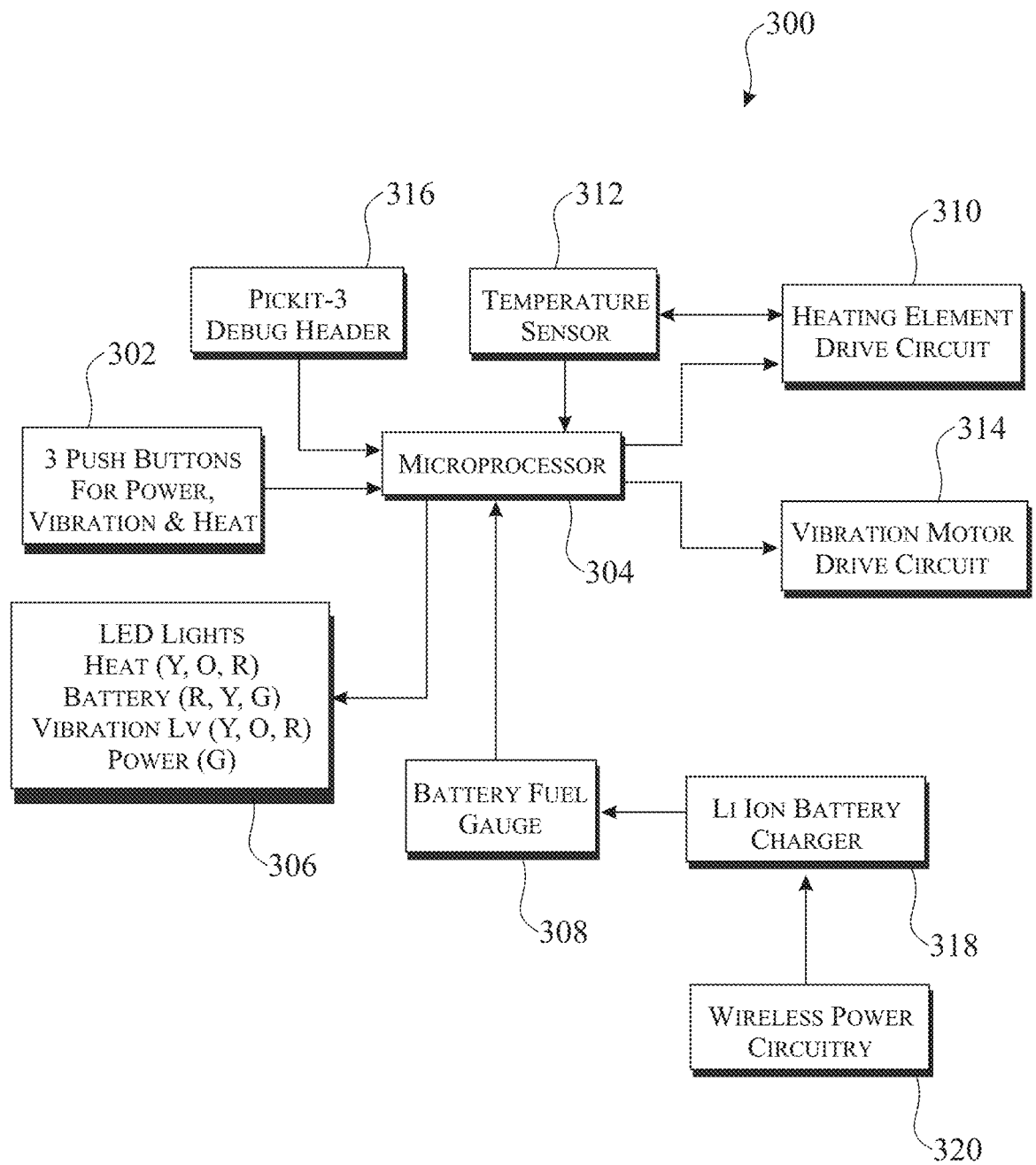
FIG. 13 presents a block diagram of operational components within the rollable apparatuses of FIGS. 1 and 9.

Referring to FIG. 13, there is illustrated a block diagram, generally designated 300, of the arrangement of operational components in each of the rollable apparatuses 100,200. The various blocks 302-320 of the block diagram 300 represent the set of components within each of the rollable apparatuses 100, 200 which cause it to operate in a safe manner as a variable speed vibrator with variable heat. By way of example, a given one of the rollable apparatuses receives control inputs from a given one of a three push button set 112, as represented by block 302. A first one 142 of the push button set 302 is used to turn on or off the power for the rollable apparatus; a second one of the push button set 302 is used to set the vibration speed; and, a third one of the push button set 302 is used to set the level of the heat. Once the rollable apparatus is powered up by activating the power pushbutton, a microprocessor, represented by block 304, on the PCB 140 turns on the appropriate one of the Light Emitting Diode (LED) lights 146, as represented by block 306, indicating that the rollable apparatus is active.

Next, the microprocessor 304 of the rollable apparatus checks the electrical charge level of the batteries 108 by interrogating a battery fuel gauge, as represented by block 308. If the batteries contains insufficient electrical charge to operate the microprocessor 304, the appropriate one of the LED lights 306 is then turned on to indicate low or no battery electrical charge level. The microprocessor 304 then suspends activity until the battery electrical charge level is brought up to the required minimum operating level. If the batteries 108 contain sufficient electrical charge to operate, the microprocessor 304 then enters a wait state and suspends operation while waiting for inputs from either the heat control push button of the set 112/302 or the vibration control push button of the set 112/302.

If the heat control push button of the set 112/302 is depressed, the microprocessor 304 turns on the heating element 104 via its heating element drive circuit, as represented by block 310, to heat the housing 102 of the rollable apparatus to a temperature level within a range of temperatures as desired by the user. The temperature of the heating element 104 is monitored by a temperature sensor, as represented by block 312. A software control loop executing inside the microprocessor 304 uses the output of the temperature sensor 312 and a pulse width modulation circuit inside the microprocessor to regulate the temperature of the heating element 104 via the heating element drive circuit 310. The temperature sensor 312 also monitors the temperature of the rollable apparatus as a safety feature. The rollable apparatus is automatically powered off if its temperature exceeds a safety threshold.

If the vibration control push button of the set 112/302 is depressed, the microprocessor 304 turns on the vibration-inducing motor 106 via a vibration motor drive circuit, as represented by block 314, to the level desired by the user. Software and a pulse width modulation circuit inside the microprocessor 304 drives a FET in the vibration-inducing motor drive circuit 314 to turn the vibration on and off. This adjusts the speed of the vibration-inducing motor 106, thereby regulating the amount of vibration emanating from the rollable apparatus.

The LED lights 306 mounted on the rollable apparatus are used to indicate the level of heat, the level of vibration and the remaining battery electrical charge life. Another component shown in the block diagram 300 is a debug header, as represented by block 316, which is used to program the microprocessor and to debug the software during initial testing. However, this component is not accessible to the user.

Figure 12:
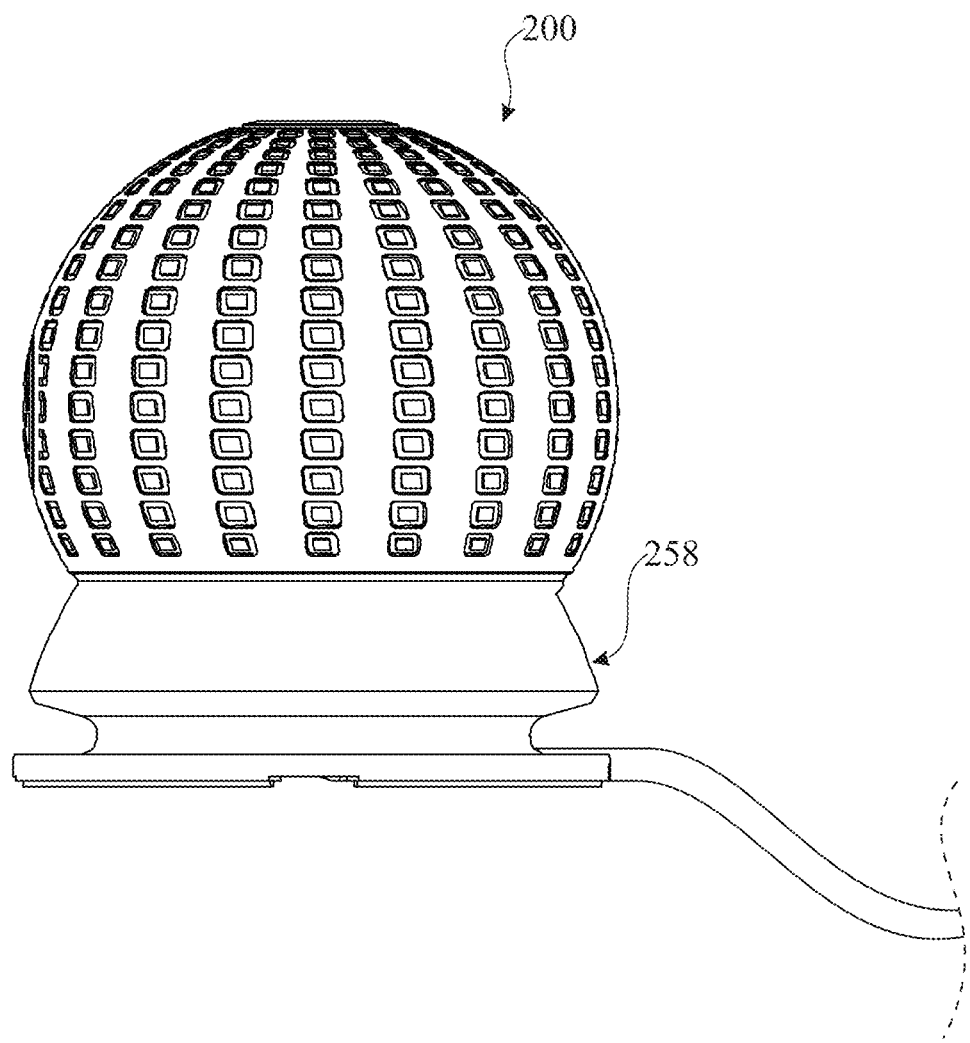
FIG. 12 presents a side elevation view of the rollable apparatus of FIG. 9 showing the rollable device supported on a base station.

Also, as mentioned earlier, the rollable apparatus contains and is powered by a lithium ion battery set 108, which are recharged via a wireless charging circuit of a Li ion battery charger, as represented by block 318. The rollable apparatus resides in a base station 258, as seen in FIG. 12, when not in use. The base station 258 contains a wireless power circuit 320 which is capable of converting wireless energy (radio waves) into DC voltages for the Li-ion battery charger 318 which monitors and charges the Li-ion batteries 108. The battery fuel gauge 308 monitors the battery charge and the microprocessor 304 queries the battery fuel gauge 308 to determine the battery charge. The microprocessor 304 then turns on the appropriate one of the LED lights 306 with the appropriate color to indicate the remaining charge on the batteries 108 for the user.

In summary, the goal of the rollable apparatuses 100, 200 is to aid in soft tissue release and loosening of muscle tissue to facilitate lengthening (increase in range of motion) and healing. Each apparatus accomplishes this by inclusion of an oscillating (vibrating/pulsing) component in combination with a heating component. The ability to provide this combination is a significant feature of the present invention. Potential applications for use of the rollable apparatuses 100, 200 include, but are not limited to, muscle tension release, myofascial release and lengthening, increased blood flow to surrounding tissues, and increased activation of tissues when used on a high oscillation setting. The above-described rollable apparatuses 100, 200 are implemented as a ball of spherical shape. By way of example, but not limitation, each apparatus is preferably between four to six inches in diameter; however, other sizes and geometries are also contemplated and considered to be within the intended scope of the invention. For example, in an alternatively implementation, the rollable apparatus may be implemented as a roller of cylindrical shape, in varying sizes (e.g., denoted "small," "medium," and "large"), and capable of selective vibration/oscillation within a desired range of frequencies.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A rollable apparatus, comprising:
    a housing being annular in shape;
    a heating element mounted about the exterior of said housing, wherein said heating element comprises an annular band and a plurality of arcuate strands attached to said band in a laterally spaced-apart array that matches an array of grooves formed in the exterior of said housing such that said heating element strands fit within said array of grooves formed in said housing exterior;
    a vibration-inducing motor mounted in the interior of said housing and attached thereto;
    at least one battery mounted in the interior of said housing for powering said heating element to heat said housing to temperature level within a given temperature range and for powering said vibration-inducing motor to induce oscillatory motion in said housing; and a set of user controls mounted on said housing to control said heating element and said vibration-inducing motor.

2. The rollable apparatus of claim 1 further comprising a microprocessor mounted in said housing for receiving inputs from said set of user controls operated by a user to control respective operation of said heating element and vibration-inducing motor.

3. The rollable apparatus of claim 2 further comprising a temperature sensor in said housing for sensing and inputting temperature status of said heating element to said microprocessor for controlling operation of said heading element.

4. The rollable apparatus of claim 2 wherein said set of user controls comprises a set of user-operated push buttons for activating inputs to said microprocessor and a plurality of LED lights controlled by said microprocessor for indicating the status of said heating element and vibration-inducing motor.

5. The rollable apparatus of claim 2 further comprising a battery fuel gauge for indicating the status of battery electrical charge to said microprocessor, and a battery charger operable for increasing the electrical charge of said battery.

6. The rollable apparatus of claim 1 further comprising a skin of pliable cushioning material covering said housing and said heating element thereon.

7. The rollable apparatus of claim 1 wherein said housing comprises front and rear housing portions, said front housing portion has a rear annular rim and said rear housing portion has a front annular rim that faces toward and fits with said rear annular rim of said front housing portion.

8. The rollable apparatus of claim 7 wherein said rear housing portion of said housing has a plurality of rear lugs formed on, and protruding radially inward from, the interior of said rear housing portion at angular and circumferentially-spaced relationships to one another and proximate said front annular rim such that said rear lugs terminate substantially flush with said front annular rim.

9. The rollable apparatus of claim 8 wherein said front housing portion of said housing has a plurality of front lugs formed on, and protruding radially inward from, the interior of said front housing portion at angular and circumferentially-spaced relationships to one another and proximate said rear annular rim such that said front lugs terminate substantially flush with said rear annular rim and said front lugs on said front housing portion are alignable with said rear lugs on said rear housing portion when said front and rear housing portions are fitted to one another.

10. The rollable apparatus of claim 9 wherein said housing also comprises a plurality of fasteners securing aligned pairs of said front and rear lugs together and thereby detachably attach said front and rear housing portions to one another.

11. A rollable apparatus, comprising:
a housing being annular in shape;
a heating element mounted about the exterior of said housing;
a vibration-inducing motor mounted in the interior of said housing and attached thereto;
at least one battery mounted in the interior of said housing for powering said heating element to heat said housing to a temperature level within a given temperature range and for powering said vibration-inducing motor to induce oscillatory motion in said housing;
a set of user controls mounted on said housing to control said heating element and said vibration-inducing motor;
a front cover removably mounted on the exterior of said housing so as to cover said set of user controls; and
rear and front roller elements mounted to said end of said housing and to said front cover such that said front cover must be removed to gain access to said set of user controls.

12. The rollable apparatus of claim 11 further comprising a grip handle device being detachable and attachable to said rear and front roller elements to enable a user to grasp and carry said rollable apparatus.

13. The rollable apparatus of claim 11 further comprising a microprocessor mounted in said housing for receiving inputs from said set of user controls operated by a user to control respective operation of said heating element and vibration-inducing motor.

14. The rollable apparatus of claim 11 wherein said heating element comprises an annular band and a plurality of arcuate strands attached to said band in a laterally spaced-apart array that matches an array of grooves formed in the exterior of said housing such that said heating element strands fit within said array of grooves formed in said housing exterior.

15. The rollable apparatus of claim 14 further comprising a skin of pliable cushioning material covering said housing and said heating element thereon.

16. The rollable apparatus of claim 11 wherein said housing comprises front and rear housing portions, said front housing portion having a rear annular rim and said rear housing portion having a front annular rim that faces toward and fits with said rear annular rim of said front housing portion.

17. A rollable apparatus, comprising:
a housing being annular in shape;
a heating element mounted about the exterior of said housing, wherein said heating element comprises an annular band and a plurality of arcuate strands attached to said band in a laterally spaced-apart array that matches an array of grooves formed in the exterior of said housing such that said heating element strands fit within said array of grooves formed in said housing exterior;
a vibration-inducing motor mounted in the interior of said housing and attached thereto;
at least one battery mounted in the interior of said housing for powering said heating element to heat said housing to a temperature level within a given temperature range and for powering said vibration-inducing motor to induce oscillatory motion in said housing;
a set of user controls mounted on said housing to control said heating element and said vibration-inducing motor;
a roller element mounted to one end of said housing; and
a cover mounted to an opposite end of said housing and having an opening recessed centrally therein through which to gain access to said set of user controls such that said cover need not be removed to access said set of user controls.

18. The rollable apparatus of claim 17 further comprising a glove handle device detachably attachable to said roller element at a respective one of the opposite ends of said housing for receiving a hand of a user to grasp and direct the rollable apparatus in contact with areas of the body of a user for application of a treatment thereto.

19. The rollable apparatus of claim 17 further comprising a microprocessor mounted in said housing for receiving inputs from said set of user controls operated by a user to control respective operation of said heating element and vibration-inducing motor.

* * * * *